(12) United States Patent
Alexe et al.

(10) Patent No.: US 8,165,973 B2
(45) Date of Patent: Apr. 24, 2012

(54) METHOD OF IDENTIFYING ROBUST CLUSTERING

(75) Inventors: Gabriela Alexe, Medford, MA (US); Gyan V Bhanot, Princeton, NJ (US); Ajay K Royyuru, Congers, NY (US)

(73) Assignee: International Business Machines Corporation, Armonk, NY (US)

( * ) Notice: Subject to any disclaimer, the term of this patent is extended or adjusted under 35 U.S.C. 154(b) by 1143 days.

(21) Appl. No.: 11/764,575

(22) Filed: Jun. 18, 2007

(65) Prior Publication Data

US 2008/0313135 A1  Dec. 18, 2008

(51) Int. Cl.
*G06F 15/18* (2006.01)
*G06F 17/00* (2006.01)
*G06N 5/00* (2006.01)

(52) U.S. Cl. .......................... 706/12; 706/45
(58) Field of Classification Search .............. 706/45–47, 706/12
See application file for complete search history.

(56) References Cited

U.S. PATENT DOCUMENTS

| | | | | |
|---|---|---|---|---|
| 2002/0090631 A1* | 7/2002 | Gough et al. | | 435/6 |
| 2006/0063156 A1* | 3/2006 | Willman et al. | | 435/6 |
| 2007/0174268 A1* | 7/2007 | Posse et al. | | 707/5 |
| 2008/0014646 A1* | 1/2008 | Kuroda et al. | | 706/21 |
| 2008/0058659 A1* | 3/2008 | Al-Abed et al. | | 600/509 |

OTHER PUBLICATIONS

Alexe,G. et al. "Enrichment of longevity phenotype in mtDNA haplogroups D4b2b, D4a, and D5 in the Japanese population" Springer. Human Genetics, vol. 121, No. 3-4. pp. 347-356. Published online: Feb. 17, 2007. DOI 10.1007/s00439-007-0330-6.*
Alexe et al. "Data Perturbation Independent Diagnosis and Validation of Breast Cancer Subtypes Using Clustering and Patterns" Cancer Informatics Online 2006. pp. 243-274.*
Ma et al. "A two-gene expression ratio predicts clinical outcome in breast cancer patients treated with tamoxifen" Cancer Cell, vol. 5. Jun. 2004. pp. 607-616.*
Misra,J. "Quantitative Methods for Linking Transcriptional Profiles to Physiology" Ph.D. Thesis, Massachusetts Institute of Technology, 2004. pp. 1-126.*
Alexe,G. et al. "Analysis of breast cancer progression using principal component analysis and clustering" Journal of Biosciences. Aug. 2007, Springer India / Indian Academy of Sciences. pp. 1027-1039.*

(Continued)

*Primary Examiner* — Jeffrey A Gaffin
*Assistant Examiner* — Benjamin Buss
(74) *Attorney, Agent, or Firm* — Scully, Scott, Murphy & Presser, P.C.; Vazken Alexanian

(57) ABSTRACT

A method of finding robust clusters comprises the use of principal component analysis and consensus ensemble clustering. In another aspect, the method may comprise normalizing a data set; identifying attributes of the data set that contribute to most of variation in the normalized data set; selecting data having the attributes that contribute to most of variation in the normalized data set; identifying a plurality of clusters from the selected data using consensus ensemble clustering; and identifying robust clusters from the plurality of clusters. The method can be used in healthcare and life science.

20 Claims, 8 Drawing Sheets

OTHER PUBLICATIONS

Oba, S. et al. "A Bayesian missing value estimation method for gene expression profile data" Bioinformatics, vol. 19 No. 16. 2003. pp. 2088-2096. DOI: 10.1093/bioinformatics/btg287.*

Strehl, A. et al. "Cluster Ensembles—A Knowledge Reuse Framework for Combining Multiple Partitions" Journal of Machine Learning Research 3. Published Dec. 2002. pp. 583-617.*

Sturn, A. "Cluster Analysis for Large Scale Gene Expression Studies" Master Thesis. Institute for Biomedical Engineering, Graz University of Technology and the Institute for Genomic Research. Rockville, Maryland. 2000. 82 pages.*

Dalgin, G.S. et al. "Portraits of breast cancer progression" BMC Bioinformatics, vol. 8. Aug. 6, 2007. pp. 1-16.*

Alexe, G. et al. "High Expression of Lymphocyte-Associated Genes in Node-Negative HER2+ Breast Cancers Correlates with Lower Recurrence Rates" Cancer Research. Published online Nov. 15, 2007. pp. 10669-10676. doi:10.1158/0008-5472.CAN-07-0539.*

Alexe, G. et al. "PCA and Clustering Reveal Alternate mtDNA Phylogeny of N and M Clades" Journal of Molecular Evolution, vol. 67, No. 5. Springer. Published online Oct. 15, 2008. pp. 465-487. DOI 10.1007/s00239-008-9148-7.*

Alexe, G. et al. "Breast Cancer Stratification from Analysis of Micro-Array Data of Micro-Dissected Specimens" Genome Inform. 2007. pp. 130-140.*

Arkat, J. et al. "Applying simulated annealing to cellular manufacturing system design", International Journal of Advanced Manufacturing Technology, vol. 32 (Mar. 2007), pp. 531-536. Published online Mar. 30, 2006. DOI:10.1007/s00170-005-0358-5.*

Hofmann, T. et al. "Multidimensional Scaling and Data Clustering", Advances in Neural Information Processing Systems 7, MIT Press, 1995. 8 pages.*

* cited by examiner

US 8,165,973 B2

METHOD OF IDENTIFYING ROBUST CLUSTERING

FIELD OF THE INVENTION

The present disclosure relates generally to a method of finding robust clusters and more particularly to the use of principal component analysis and consensus ensemble clustering to identify robust clusters.

BACKGROUND OF THE INVENTION

Microarrays have the potential to identify pathways that are altered in disease. This promise has resulted in this technology being aggressively pursued by researchers, hospitals and pharmas because of the possibility that it might lead to improved understanding of the disease process, better diagnostic protocols, new drugs, and new treatment regimens.

For example, a major application of micro arrays has been to the analysis of cancer. The focus has been on identifying genes that are altered in the initiation, progression and metastasis of cancer. Such analysis is confounded by the fact that most cancers are highly heterogeneous, micro-array signals are noisy and there is a large variation in the "normal" levels of most genes. A major cause of the lack of success in treatment is that tumors with similar histopathology signatures have divergent clinical courses and prognosis. Many studies have been done motivated by the hope that molecular signatures can be found that are more correlated with outcome than the currently prevalent histological categories and treatment protocols. Such signatures would provide insight into processes critical to tumor development and lead to potential therapeutics or targets.

However, identification of the subtle signals that identify the disease phenotypes and its progression requires robust techniques. Further, considering the pathological heterogeneity of cancer, it seems reasonable to ask whether these cancer phenotypes are robust and homogeneous and whether they can be reliably stratified into sub-subtypes. Although a number of markers for each of these phenotypes are determined by several different studies, and the cohorts differ in each study, a consensus set of markers that would apply to different types of cancer patients, e.g. breast cancer is still not available.

It would be highly desirable to provide a new robust technique to analyze micro array data, for example, one that uses of principal component analysis and consensus ensemble k-clustering to identify robust clusters and gene markers in the data.

SUMMARY OF THE INVENTION

A method of finding robust clusters is provided. The method in one aspect may comprise identifying patterns of variation in the data, applying consensus ensemble clustering to said identified variations, and identifying robust clusters. In one aspect, the step of identifying patterns includes performing principal component analysis to identify patterns of variation in the data.

A method of finding robust clusters in data in another aspect may comprise normalizing a data set, identifying attributes of the data set that contribute to most of variation in the normalized data set, selecting data having the attributes that contribute to most of variation in the normalized data set, identifying a plurality of clusters from the selected data using consensus ensemble clustering, and identifying robust clusters from the plurality of clusters.

A program storage device readable by machine, tangibly embodying a program of instructions executable by the machine to perform the above method steps is also provided.

Further features as well as the structure and operation of various embodiments are described in detail below with reference to the accompanying drawings. In the drawings, like reference numbers indicate identical or functionally similar elements.

DETAILED DESCRIPTION

Figure 1:
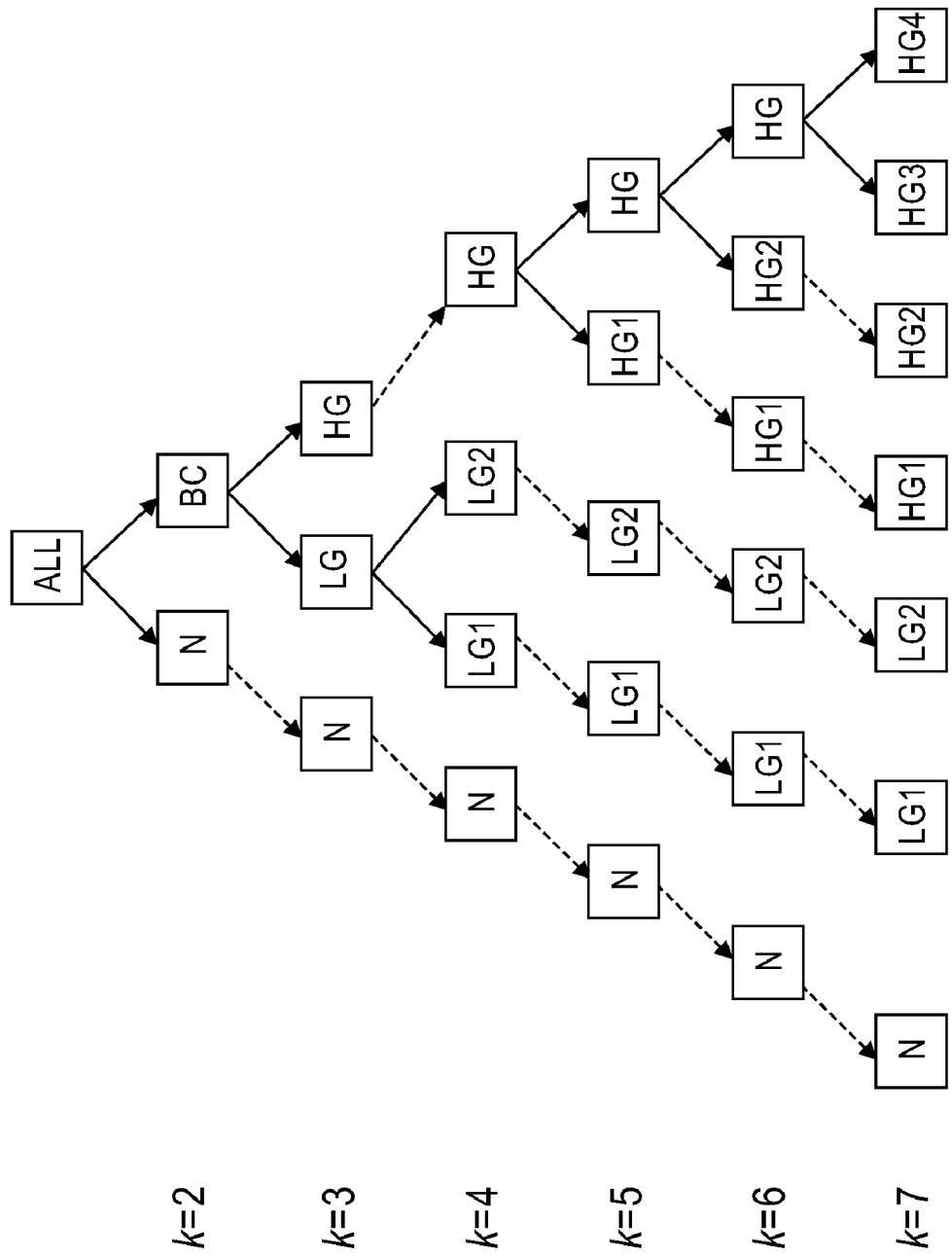
FIG. 1 illustrates an example data divided into different clusters using the 207 genes identified by PCA and applying consensus ensemble K-clustering.

A method of finding robust clusters in data is provided. The method in one aspect may be used to identify gene markers. An embodiment of the method of finding robust clusters in data may comprise normalizing a data set, finding the eigenvalues and eigenvectors of the matrix representing normalized data set, identifying attributes that contribute the most to variation in the data from coefficients of these eigenvectors, applying consensus ensemble clustering, and identifying robust clusters, wherein missing entries may be robustly estimated or imputed if necessary.

In one aspect of the invention, patterns of variations in the data are identified via different kinds of method. For example, Principal Component Analysis (PCA) can be applied. Principal components analysis (PCA) is a statistical technique for simplifying a dataset, by reducing multidimensional datasets to lower dimensions for analysis. See eg, Wall, Michael E., Andreas Rechtsteiner, Luis M. Rocha. "Singular value decomposition and principal component analysis". in *A Practical Approach to Microarray Data Analysis*. D. P. Berrar, W. Dubitzky, M. Granzow, eds. pp. 91-109, Kluwer: Norwell, M A (2003). LANL LA-UR-02-4001, incorporated by references herein. Technically, PCA is a linear transformation that transforms the data to a new coordinate system such that the greatest variance by any projection of the data comes to lie on the first coordinate (called the first principal component), the second greatest variance on the second coordinate, and so on. PCA can be used for dimensionality reduction in a dataset while retaining those characteristics of the dataset that contribute most to its variance, by keeping lower-order principal components and ignoring higher-order ones. Such low-order components often contain the "most important" aspects of the data.

One embodiment of the present invention restricts the data to attributes identified by PCA and creates several training sets, that is, testing data sets by dividing data repeatedly into two partitions in a n:1 ratio, to determine the optimum number of clusters over data sets using a metric, where n is an integral number, such as 1, 2, 3, 4, etc.

In another aspect of the invention, for each method, an agreement matrix is created. The rows and the columns in the agreement matrix are associated to the samples in the data and the entry corresponding to a pair of samples i and j represent the fraction of times the pair of samples i, j occurs in the same cluster across the bootstrap experiments.

In one embodiment, the samples are sorted using simulated annealing to convert the agreement matrix into block diagonal form so that the samples that are in the same cluster have high fractions in blocks along the diagonal.

An agreement matrix may be created across clustering techniques for the clusters found from each technique and simulated annealing reapplied to find the best blocks of samples along the diagonal. These blocks are then the final clusters.

In another aspect, a method of the present invention normalizes the data by first applying a robust nonlinear local regression method, and then applying a global normalization procedure, which may include subtracting the median of each data across the arrays. The may be collected by existing information or collected from at least one clinical sample.

Any clustering techniques, for example, agglomerative, hierarchical, probabilistic, and the like, can be used in this method. Unsupervised clustering algorithms divide data into meaningful groups or clusters such that the intra-cluster similarity is maximized and the inter-cluster similarity is minimized.

Clustering is a non-polynomial hard problem. However, many heuristic methods exist and they can be categorized into hierarchical, partitioning and grid-based methods. In the study all these methods are applied in an unsupervised way to the data, i.e. without assuming a predefined label on the objects to be classified. Unsupervised clustering is known to produce unstable solutions, which are sensitive to various data parameters and/or perturbations and to the clustering techniques used. A relatively recent solution, which corrects for this instability is consensus ensemble clustering.

Given several methods of clustering data, consensus ensemble clustering finds a combination of these methods, which improves the quality of the individual methods. Preferably, ensemble consensus clustering integrates the results of various clustering techniques across sample data perturbations into a pair wise agreement matrix, which is used to partition the samples into the optimum number of clusters.

In one embodiment. A method of finding robust cluster may include the following steps:

Step 1. A full dataset is created from the imputed or estimated data restricted to the multiple significant genes identified by PCA. As an example, partial datasets came from bootstrapping the samples, partial from bootstrapping genes and partial by first projecting the data on bootstrapped genes and then by further bootstrapping on samples.

Step 2. The optimal number of clusters $k_{opt}$ is inferred (a priori) using gap statistic and the silhouette scores.

Step 3. k=2, ..., $k_{opt}$ clusters are created using representative methods from the three major classes:
  Partitioning: partition around medoids (PAM), k-means and graph partitioning;
  Agglomerative: hierarchical clustering based on average linkage, complete linkage and Ward metric as well as bagglo;
  Probabilistic: expectation maximization (EM) method, entropy-based-clustering (ENCLUST), clustering on subsets of attributes (COSA).

Step 4. Each clustering method is applied multiple times with different parameter initialization on the full dataset, and once on each of the full datasets from Step 1. From the resulting clusters, an agreement matrix is constructed of size $N_{sample} \times N_{sample}$ for each method, whose entries $m_{ij}$ represent the fraction of times a pair of samples (i,j) occur in the same cluster out of the number of times the pair is selected in the said datasets. Here $N_{sample}$ denotes the number of samples in the dataset.

Step 5. For each k, the agreement results of Step 4 are averaged across the clustering techniques. The samples are then sorted such that those with the highest pairwise agreement appeared along the diagonal of the agreement matrix in k blocks. Simulated annealing is applied to find the k optimal clusters for which the average internal similarity (within each cluster) minus the average pairwise similarity (between all pairs of clusters) has a local maximum value.

In one aspect, a consensus ensemble clustering is used to project the data on genes to robustly identify k=2, 3, ... $k_{opt}$ clusters wherein the clustering enables visualization of the disease at varying levels of granularity.

The consensus ensemble clustering may comprise: (1) generating a collection of clustering solutions using different methods applied to many perturbations of the data, and (2) implementing a consensus function for combining the clusters found to produce a single output clustering of the data.

In one embodiment, the cluster generation approach starts by dividing the data into two clusters. The normal samples form one cluster and the disease samples form another cluster In another aspect of the invention, a full set of genes on the samples is used after each k level clustering to find a large pool of genes that distinguish disease classes within and between clusters to ensure sensitivity to subtle signals that may be present and at least one sub-class of genes is further identified on this larger pool of genes for each k. This nonstringent selection is motivated by the expectation that the key genes altered in disease pathways most likely change their expression levels in subtle ways.

Further separating sub-clusters can be applied by a strong set of markers, which are able to distinguish them with sensitivity and specificity in about 80%-100% range and identifying the genes and pathways that mark disease progression in each sub-cluster.

The method in one aspect may produce results in detailed assignment protocols for all robust groups in the data with a predictive accuracy exceeding about 80%, preferably exceeding about 85%, and more preferably exceeding about 90%.

In one aspect, the markers are chosen to discriminate between two classes: one class is the group of interest and the other class is group of no interest. More than two classes can also be discriminated according to the method.

In one aspect, the method of the present disclosure may be applied in analyzing nucleotide polymorphism data wherein said data is generated either by the public or by clinic sample.

The method of the present disclosure may further create a tree of population events for groups that emerge from a bottleneck or founder event wherein the tree is haplogroups and rooting the bifurcating tree using Poisson dynamics to find an internal node, which is equidistant from the leaves.

The method of the present disclosure may be applied in the fields of life science and healthcare. For example, the method may be applied in identifying generic profile of a patient in phenotype discovery. Phenotype discovery may be a drug efficiency analysis or a disease risk.

In another aspect, the method may be applied in analysis of gene-array or mutation data, e.g. data where rows are patients and the columns are gene or protein levels or mutations seen in the patients, to find how the patients cluster with respect to these attributes wherein cluster can identify their generic profile and would be applicable to phenotype discovery, such as drug efficiency analysis, disease risk and the like. The disease, for example, can be various kinds of cancer, heterogeneous cancers, such as Lung cancer, Beast cancer, kidney cancer and the like.

Furthermore, the method may be able to identify portraits of breast cancer progression and preferably the different stages of breast cancer, for example, atypical ductal hyperplasia or ADH, ductal carcinoma in situ or DCIS, and invasive ductal carcinoma or IDC.

Breast cancer (BCA), is a common and extensively heterogeneous disease affecting women of all ages. Its occurrence correlates with expression levels of a number of hormone receptors, most notably estrogen (ER), progesterone (PR) and Her2neu (ERBB2). Breast cancer tissue is grossly classified into two major phenotypes depending on the presence of estrogen receptors. Tumors with high or low estrogen response are called estrogen positive or negative (or ER+, ER−) respectively. These groups are sometimes further stratified with respect to ERBB2 and PR. Patients with ER or PR positive tumors tend to have better prognosis and are more likely to respond to chemotherapy and hormone treatment (e.g., tamoxifen) than those with ER and PR negative tumors. Tumors which are PR positive, but ER negative, usually have poor prognosis. The over-expression of ERBB2, which occurs in 25-30% of the breast cancer cases, is often associated with more aggressive tumors, poor prognosis and mixed treatment results.

Ductal carcinoma in situ (DCIS) is a noninvasive, precancerous condition in which abnormal cells are found in the lining of a breast duct. The abnormal cells have not spread outside the duct to other tissues in the breast. This is early-stage breast cancer. Some experts consider DCIS a "precancerous" condition. Almost all women with DCIS can be successfully treated, and no evidence suggests that DCIS affects a woman's life span. In some cases, DCIS may become invasive cancer and spread to other tissues, although it is not known at this time how to predict which lesions will become invasive.

Recent gene array studies suggest that the breast cancer phenotype can be classified into four categories: Luminal A, Luminal B, ERBB2+ and Basal. The first two are estrogen positive and the latter two estrogen negative. Luminal and basal-like breast cancers correspond to two distinct types of epithelial cells found in normal mammary gland. These subtypes show a different clinical course and response to therapeutic agents. In particular the Luminal A phenotype has a better prognosis than Luminal B Basal phenotype, most common in inherited breast cancer (which has mutations in the BRCA1 and BRCA2 genes) is known to be highly aggressive. The cDNA microarray study suggests that these categories used simple hierarchical clustering to identify gene markers specific to each phenotyope. The basal-like subtype is characterized by high expression of keratins 5 and 17, laminin, and fatty acid binding protein 7, whereas ERBB2+ subtype is characterized by high expression of several genes in the ERBB2 amplicon at 17q22.24 including ERBB2 and GRB7.

Infiltrating ductal carcinoma (IDC) is the most common invasive breast cancer, accounting for 70 percent of all cases. A very hard lump that has irregular borders and seems anchored in surrounding tissues is characteristic of infiltrating ductal carcinoma. The skin over the area or the nipple may retract (pull in). On mammography, there are often microcalcifications found in the tumor area, since this tumor has a history of internal cell death (necrosis). The tumor varies in size and cell division time, with some cells growing more rapidly than others. These classifications are extensively used by clinicians, to make decisions about the appropriate level and nature of treatment. It is therefore of great interest to correlate the ER, PR, Her2 status of the tumors with the underlying disease mechanisms. In particular, it is desirable to understand the sequence of steps that give rise to different phenotypes observed in BCA and if possible, elaborate the underlying pathways and the steps that lead to their initiation. Such an understanding would be invaluable in determining adequate testing procedures and determining appropriate treatment.

The method in another aspect may also be used in Consensus Ensemble Clustering Reveals Novel mtDNA Phylogeny for the N Clade Constructing Phylogeny. It is generally agreed that modern humans emerged from Africa between 70 and 50 kYBP. However, details of their evolution phylogeny and migratory routes are still under debate. Depending on which samples and mutations are used, different techniques give different phylogenies. All algorithm based techniques make explicit assumptions, which may not necessarily be valid (e.g., parsimony minimizes the number of branches and mutations, ML maximizes a likelihood function etc). Such assumptions, to a large extent, predetermine the nature of the resulting tree. Finally, most techniques are restricted by the computational complexity to small sample sizes and limited numbers of mutations and consequently, there is a risk of missing the global structure of the data entirely.

As an example, a new technique that identifies all robust mutations in the data and simultaneously analyzes all 1737 available mtDNA samples in the public record to infer haplogroup phylogeny is described and applied. Principal component analysis (PCA) is used to identify the mutations that represent most of the variation in the data. Using these mutations, robust clusters are created using techniques which maximize the homogeneity of samples within clusters and the heterogeneity of samples between clusters; dividing the data into k=1, 2, . . . $k_{max}$ clusters using unsupervised consensus ensemble k-clustering (UCEkC). This technique averages over probabilistic, agglomerative and hierarchical clustering methods and many data perturbations to build an agreement matrix to determine a robust set of clusters and their distinguishing mutations. The optimum number of clusters ($k_{max}$) is inferred from the silhouette score and gap-statistics. For statistical accuracy, in one embodiment, the clusters have a minimum sample size. The robustness and statistical significance of the clusters and mutations is validated by averaging over ten 2:1 training/test bootstrapped datasets on which the complete clustering analysis is repeated. Only 90% or higher sample assignments into clusters and predictive mutations are accepted.

Mitochondria travel as a single locus, in complete linkage disequilibrium and without recombination. Imagine that a positively selected mutation appears on an autosomal chromosome. It would tend to amplify the mitochondrial mix of samples in which it becomes established and over time, by drift, would tend to amplify one particular mtDNA group which remained as a consequence of coalescence. As has been shown recently such selective sweeps on intDNA have indeed happened, not just in humans but across many species of animals. A consequence of such sweeps is the disappearance of the correlation between effective population size and mtDNA genetic diversity. This means that selective mutations on autosomes will not just amplify the largest mtDNA haplogroup; rather, any haplogroup, however inconsequential, is a potential candidate for amplification.

The notion of amplification of mtDNA because of selective sweeps on autosomes is called "genetic draft". It provides the following alternate explanation for the appearance of haplogroups: Haplogroups are triggered by selective mutations on autosomes. This results in an amplification of the mtDNA in the individuals in which the autosomal mutation spreads. Over time, this leads to an amplification of some mtDNA sequences and later, via the usual process of genetic drift, to the establishment of a unique haplogroup signature for the group or a subgroup. A sequence of such sweeps in two geographically isolated haplogroups (such as the "European R clade" and the "Eastern R clade") which evolve under different selection pressures, would tend to create sub-haplogroups in each group which would be very homogeneous within a geography but very different across geographies. This precisely describes the situation on the N lade tree, where samples from the "R haplogroup" are split across Europe and Asia.

Migrating groups moving from Africa to colder northern climates must have been subject to selection pressure from changes in diet, new diseases, adaptation to cold, etc. These selection pressures would be different in different geographies. These pressures are certainly different in Europe and Eurasia. If selective mutations on autosomes created recent (<20kYBP) haplogroups, then on the scale of complete mtDNA sequences, the groups in geographic proximity would tend to become more similar than those geographically far apart. This is exactly what the clustering analysis here finds because it places groups closer in geographic location also closer on the phylogeny.

Referring back to the example of using the method of the present disclosure in identifying cancerous cells, gene markers may be determined into two types within the data:

gene markers characteristic for each subgroup (cluster) identified in the data;

gene markers for cancer progression within each subgroup identified in the data.

In a cancer example, the gene markers characteristic for each cancer subgroup are determined as those markers which discriminate between the cancer samples in the subgroup and all the cancer samples not included in the subgroup. For each gene, it is computed a non-parametric statistic called Signal-to-Noise (SNR) as the ratio of the difference of the mean of the samples in the subgroup and the mean of the samples not included in the subgroup divided by the sum of the standard deviations in the subgroup and outside the subgroup, respectively. A p-value for the SNR statistic is computed based on 100 permutations of the sample id's. The pool defined by those genes for which the permutation p-value of the SNR score is below 0.1 and the False Discovery Ratio is below 0.25 is retained.

In one aspect, the markers characteristic for the subgroup may be determined as those genes in the pool which fulfilled the following conditions:

the permutation p-value of the SNR score is below 0.05;

the gene is selected as a discriminator (based on a permutation p-value below 0.1 and a FDR below 0.25) for 75% of 100 data instances obtained by bootstrapping the samples;

the gene is selected in top 25% to leave-one-out experiments by support vector machines (linear kernel) and weighted voting classifiers calibrated to have a performance of at least 75% sensitivity and 75% specificity.

The gene markers for progression are determined for each subgroup in the data wherein the gene markers for progression are chosen to discriminate between different kinds of samples in the subgroup. For example, in breast cancer case the markers for progression are chosen to discriminate between the DCIS (ductal carcinomas in situ) and the IDC (invasive ductal carcinomas) samples in the subgroup.

EXPERIMENT

The following paragraphs describe the method in one embodiment as used in an experiment of microarray data.

Public data from Ma X. J. et al., "Gene Expression Profiles of Human Breast Cancer Progression", *Proc. Nat'l Acad. Sci. USA.*, 1:5974-59749 (2003) are used in this experiment. The data includes a cohort of 36 breast cancer patients of whom 31 are diagnosed with at least two out of three pathological stages of disease; atypical ductal hyperplasia or ADH, ductal carcinoma in situ or DCIS and invasive ductal carcinoma or IDC respectively. The remaining five patients are diagnosed to have pre-invasive disease (ADH). In addition, there are three healthy women who are sampled during elective mammoplasty reduction. The Normal, ADH, DCIS or IDC samples are laser capture micro-dissected in triplicate with care taken to avoid contamination between cells of different stages taken from the same patient.

There are a total of 300 samples in the Ma et al. study, each of which is analyzed in duplicate with a 12,000 gene cDNA microarray. It is determined that the "normal cells" from cancer patients are highly similar to the normal epithelium of non-cancer patients. This suggested that the "normal cells" from cancer patients could be used as a baseline to determine disease state and progression.

The data from the experiment is made available as the subset of genes, identified by linear discriminate analysis, which could distinguish "normal cells" from ADH, DCIS and IDC. Patients and genes are selected by Ma et al. only if they could discriminate between these phenotypes above a discriminate function coefficient>0.5. These datasets are downloaded from the web site at "www.aeneexnression ma.orcz". The dataset had a total of 1940 gene expression values for each of 93 samples of which 32 are Normals, 8 are ADH, 30 are DCIS and 23 are IDC. The patients are further classified by pathological analysis into 18 which have breast cancer of clinical grade 1 (low), 22 which have breast cancer of clinical grade 2 (intermediate), and 19 which have breast cancer of clinical grade 3 (high). The groups of low and high grade breast cancer contain (7, 13, 8) and (0, 17, 15) patients with ADH, DCIS and IDC phenotypes.

The following paragraphs describe overview of analysis technique in one embodiment as applied to the above experiment.

The analysis technique may include several steps. First the dataset is normalized and missing entries imputed or estimated robustly. Next, Principal Component Analysis (PCA) is used to identity genes, which account for most of the variation in the data. Next, consensus ensemble clustering is used on the projection of the data on these genes to robustly identify $k=2, 3, \ldots k_{opt}$ clusters. In one embodiment, to ensure sensitivity to subtle signals that may be present, the full set of genes on the samples are used after each k level clustering to find a large pool of genes that distinguish disease classes within and between clusters. This non-stringent selection is motivated by the expectation that the key genes altered in disease pathways most likely change their expression levels in subtle ways.

On this larger pool of genes for each k, two sub-classes of genes are identified. The first set distinguishes each cluster from its complement. The second set defines progression from non-invasive to invasive disease. Annotated databases are used to identify the functional pathways that are most representative of the clusters identified. Each of these steps is described in detail below.

Data Normalization and Imputation

The genes are normalized by first applying a robust non-linear local regression method as described in Ma et al. and then applying a global normalization procedure which includes subtracting the median of each gene across the arrays. 13 genes had missing values in 13-15% of the samples and are discarded. 105 genes had missing entries for up to 5% of the samples. These missing entries are imputed or estimated using a dynamical kNN approach.

PCA

This method identifies patterns of variation in the data. PCA is applied to the expression matrix $E_{ij}$ whose the rows are the 93 samples and whose columns are the 1927 genes. The PCA is done by a singular value decomposition of this matrix after it is centered and scaled to mean 0 and variance I per column. The eigenvectors of the highest 32 eigenvalues accounted for 85% of the variation in the data. From these, a subset of 207 genes is identified as those with coefficients in the top 25% in absolute value in these eigenvectors. This collection of genes is further used to find robust clusters in the data.

Consensus Ensemble k-Clustering

Using the genes from PCA, this method is used to group the samples by robust substructure. The method identifies robust, stable clusters in the data. It may include two parts: (1) a method which generates a collection of clustering solutions using different methods applied to many perturbations of the data, and (2) a consensus function that combines the clusters found to produce a singe output clustering of the data. The approach used in this experiment is briefly summarized below. Various clustering methods may be used as discussed below.

For example, each one or one or more of the following clustering methods may be applied to the data.

Partitioning Methods

These divide data into subsets and then use greedy heuristics, for example, iterative optimization, to reassign points between k clusters. The optimization criterion is an objective function, usually a dissimilarity measure. The following methods may be used: Partition around medoids (PAM), Kauffman et al. (1990); K-means (Hartigan J. A. et al., "A K-Means Clustering Algorithm", Applied Statistics 28:100-108 (1979); and Graph partitioning, Karypis G. et al., (2001) Criterion Functions for Document Clustering: Experiments and Analysis. UMN CS 01-040.

Agglomerative Methods

Each sample is first assigned to its own cluster. The clusters are recursively merged in pairs until a stopping criterion is fulfilled. The similarity between clusters is computed using a linkage metric which reflects the connectivity and similarity between the clusters. In one embodiment, a method of the present invention applied hierarchical clustering techniques based on the following metrics: average linkage, complete linkage and Ward metric. A hybrid biased agglomerative method (bagglo), Karypis G. et al., "Criterion Functions for Document Clustering: Experiments and Analysis. UMN CS 01-040 (2001), may be also used.

Probability Methods

The data is considered to be a sample independently drawn from a mixture model of several probability distributions and the clusters are associated with the region around the mean of each distribution such that each data point is assigned to a unique cluster. The method optimizes the log-likelihood of the data to be drawn from a given mixture model. The following methods may be used: (i) Expectation maximization (EM) method Dempster A. et al., "Maximum Likelihood from Incomplete Data Via the EM Algorithm", Journal of the Royal Statistical Society, Series B 39(1):1-38 (1977); (ii) Entropy-based-clustering (ENCLUST) (Cheng C. H. et al., "Entropy-Based Subspace Clustering for Mining Numerical Data". PhD Thesis. (1999); (iii) Clustering on subsets of attributes (COSA).

Referring back to the overall method for robust clustering, the following describe the method in one embodiment.

Step 1. 150 datasets are created from the imputed data restricted to the 207 significant genes identified by PCA. 50 datasets came from bootstrapping the samples, 50 from bootstrapping genes and 50 by first projecting the data on bootstrapped genes and ten by further bootstrapping on samples. Step 2. The optimal number of clusters $k_{opt}$, is inferred using the gap statistic. Step 3. $k=2, \ldots k_{opt}$ clusters are created using representative methods from the three major classes (partitioning, agglomerative and probabilistic) of clustering techniques. Step 4. Each clustering method is applied 50 times with different parameter initialization on the full dataset, and once on each of the 150 datasets from Step 1. From the 200 resulting clusters, an agreement matrix is constructed of size $N_{sample} \times N_{sample}$ for each method whose entries $m_{ij}$ represented the fraction of times a pair of samples (i,j) occurred in the same cluster out of the number of times the pair is selected in the 200 datasets. Simulated annealing is applied to find the k "consensus" clusters which maximized the average internal similarity and the average external dissimilarity using the cost function:

$$\sum_l \sqrt{\sum_{i,j \in Cl} dij} \Big/ \sum_l n1 \frac{\sum_{i \in Cl, j \in S} dij}{\sqrt{\sum_{i,j \in Cl} dij}}$$

where $d_{ij}=1-m_{ij}$ is the distance between the samples (i,j); $C_1, \ldots, C_k$ are the k clusters to be determined, $n_1$ is the size of cluster $C_1$ and S is the set of samples to be clustered. Step 5. For each k, the results of Step 4 are combined across clustering techniques using simulated annealing (using the method in Step 4) to average over clustering methods. The samples are then sorted such that those with the highest pair wise agreement appeared along the diagonal of the agreement matrix in k blocks.

Identification of Gene Markers within Clusters

In one embodiment, the full collection of genes on each of the clusters identified at each k by consensus ensemble clustering is used. The markers are chosen to discriminate between two classes: class 1=the group of interest (wither the entire cluster or one grade/stage of disease in the cluster), class 0=the samples not included in the group of interest (the complement of the cluster or of the grade/stage of disease in class 1). The best markers in one embodiment are identified using two steps.

Step 1. A large pool of genes which distinguished the two labeled classes are selected based on a variant of the t-test statistic called the signal to noise ratio (SNR), with a permutation p-value of 0.1 and a False Discovery Rate (FDR) of 0.5. The Signal-to-Noise (SNR) statistic looks at the difference of the means in each of the two classes scaled by the sum of the standard deviations: $SNR=(\mu_0-\mu_1)/(\sigma_0-\sigma_1)$ where $\mu_0$ is the mean of class 0 and $\sigma_0$ is the standard deviation of class 0 and so on. The t-test statistic is the same as the SNR except that the denominator is $(\sigma_0^2+\sigma_1^2)^{1/2}$. Since $(\sigma_0+\sigma_1) > (\sigma_0^2+\sigma_1^2)^{1/2}$.

SNR penalizes genes that have higher variance in each class more than those genes that have a high variance in one class and a low variance in another. This basis is particularly useful in distinguishing genes, which are altered in normal/disease or stage/grade progression. For example, in the normal/disease case, the pathway wherein the gene is involved, is working correctly in one class, and hence is regulated strictly (has low variance) while the other class, the pathway is compromised and the gene is less well regulated (has high variation).

Step 2. From the larger pool of genes from Step 1, the best genes correlated with the class label are identified using stringent criteria which combined (a) a permutation p-value of 0.05 (b) stability to sample perturbation through bootstrapping (c) stability to leave-one-out experiments in top 25% genes selected by weighted voting and support vector machines classifiers which distinguish the two classes with specificity and sensitivity above 0.75. This analysis is done using the software GenePattern from the Broad Institute of MIT.

Identification of Pathways and Biological/Functional Categories

The bioinformatics public resources DAVID (david.niaid.nih.gov/david/) (2002), iHOP (www.ihop-net.org/UniPub/iHOP/) (2004) and MatchMiner (discover.nci.nih.gov/matchminer/), as well as the functional annotation tools (14 functional annotation tools (14 functional annotation sources including KEGG and GO annotations, Biocarta pathways, linked to DAVID) and the Functional Classification Tool implemented in DAVID are used to associate biological annotations and pathways to the breast cancer markers identified in the data. The Functional Classification Tool group genes are based on functional similarity. It uses Kappa statistics (Dennis et al. Database for annotation, visualization, and integrated discovery. Genome Biol., 4, R60. (david.niaid.nih.gov/david/)), which is an index that compares the agreement against the possibility that it appeared by chance. Thus, the Kappa statistic can be thought of as the chance-corrected proportional agreement, and possible values range from +1 (perfect agreement) to 0 (no agreement above chance) to −1 (complete disagreement). The algorithm first generates a gene-to-gene similarity matrix (genes in rows and functional terms in columns) based on shared functional annotation. The matrix is made from binary entries. If a gene is annotated in a term, the term entry is 1, if not then the entry is 0. The algorithm adopts the kappa statistic to quantitatively measure the degree to which genes share similar annotation terms. The higher the value of κ, the stronger the agreement. The Fuzzy Heuristic Partition algorithm, which allows a gene to participate in more than one cluster, is used to classify highly related genes into functionally related groups.

Results

PCA

The eigenvalues of the first three PCs are 25.8, 9.97, 6.25 respectively. The first component divides the data into two groups, the normal samples and the diseased samples. The second component spreads out the diseased samples by tumor grade; a group with low grade tumors and a group with high grade tumors. 50% of the variation in the data is represented by the first 5 PCs and 85% by the first 32 PCs. 207 genes are identified as those with highest absolute value in the coefficients of the first 32 eigenvectors as representative of most of the data variation. Since the third PC has little effect and the eigenvalues decrease rapidly after the third, it is concluded that the identification of more subtle structure in the data needs better techniques than PCA. One such is consensus ensemble k-clustering and its results is described below.

Consensus Ensemble k-Clustering

Gap statistics and silhouette scores are applied to "partition around medoids" identified k=7 as the optimal value for the number of clusters in the data. The data is divided into k=2, 3, . . . , 7 clusters using the 207 genes identified by PCA and applying consensus ensemble k-clustering. The results are shown schematically in FIG. 1. Note that even though the clusters at each level are determined independently, at clustering level k+1, two clusters are always obtained from splits of a parent cluster at level k, while the remaining k−1 clusters are inherited unchanged from the previous level k. Moreover, the samples in the low and high grades are separated early (at k=3) and remained separately. This strongly suggests that disease progression is a hierarchical process and is accurately revealed by the clustering procedure.

At k=2, the samples separated into a "normal" (N) group, which contained all the normal samples and one ADH sample (from patient id 210), and a "breast cancer" (BCA) group, which contained all the remaining breast cancer samples. At k=3, the normal group is unaltered but the BCA group split into a low grade (LG) tumor group containing 18 samples labeled grade 1 and 9 samples labeled grade 2, and a high grade (HG) tumor group containing 13 samples labeled grade 2 and 19 samples labeled grade 3. As k increased progressively from 4 through 7, the LG group is split into 2 distinct subgroups (labeled LG1 and LG2 in FIG. 1) and the HG group is split into 4 distinct subgroups (labeled HG1-HG4). Table 1 shows the characteristics of the samples in these groups with respect to stage, ER, PR, Her2, node and grade status. These subgroups of LG and HG are strongly dissimilar with respect to the cluster agreement matrix, which is shown in FIG. 2.

Figure 2:
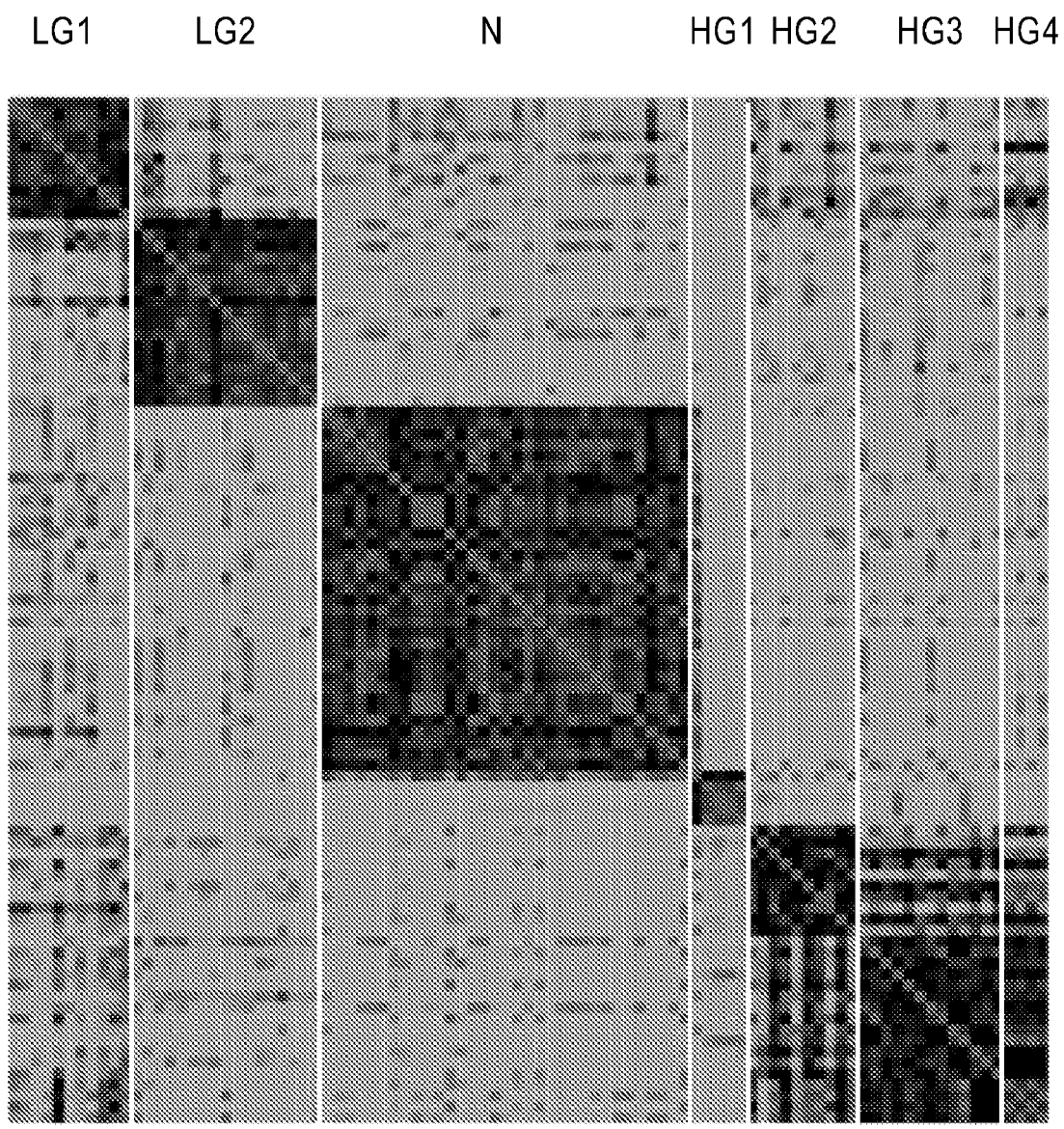
FIG. 2 illustrates the difference of subgroups of LG and HG with respect to the cluster agreement matrix in the example.

FIG. 2 shows heatmap of the agreement matrix for the k=7 level of clustering. Dark grey/light grey regions represent strong/weak agreement across clustering methods and data perturbations. The normals and the LG1 and LG2 are cleanly separated while the HG1, HG2, HG3 and HG4 separation is weaker. This explains why the optimum number of clusters using gap-statistics oscillates between 6 and 7.

Table 1 shows clinical characteristics of samples in the breast cancer subtypes. All the samples in the HG1 group are ER and PR negative, while the samples in the HG3 and HG4 subgroups are mostly ER and PR positive. The samples in the HG2 group have mixed ER and PR signatures. This might explain the strong dissimilarity between HG1 and the other HG subgroups. Almost all the samples in the LG group are ER and PR positive.

TABLE 1

| Cluster level | | | Stage | | | | ER | | | PR | | | Her2 | | | Node | | Grade | | |
| --- | --- | --- | --- | --- | --- | --- | --- | --- | --- | --- | --- | --- | --- | --- | --- | --- | --- | --- | --- | --- |
| k | Group | Size | ADH | DCIS | IDC | N | Pos | Neg | ND | Pos | Neg | ND | Pos | Neg | ND | Pos | Neg | 1 | 2 | 3 |
| 2 | N | 33 | 1 | 0 | 0 | 32 | 26 | 5 | 2 | 23 | 8 | 2 | 5 | 21 | 5 | 22 | 10 | 11 | 11 | 10 |
|   | BCA | 60 | 7 | 30 | 23 | 0 | 47 | 10 | 3 | 42 | 15 | 3 | 10 | 37 | 9 | 44 | 14 | 18 | 22 | 19 |
| 3 | LG | 28 | 7 | 13 | 8 | 0 | 26 | 0 | 2 | 21 | 5 | 2 | 4 | 18 | 6 | 20 | 8 | 18 | 9 | 0 |
|   | HG | 32 | 0 | 17 | 15 | 0 | 21 | 10 | 1 | 21 | 10 | 1 | 6 | 19 | 3 | 24 | 6 | 0 | 13 | 19 |

TABLE 1-continued

| Cluster level | | | Stage | | | | ER | | | PR | | | Her2 | | | Node | | Grade | | |
|---|---|---|---|---|---|---|---|---|---|---|---|---|---|---|---|---|---|---|---|---|
| k | Group | Size | ADH | DCIS | IDC | N | Pos | Neg | ND | Pos | Neg | ND | Pos | Neg | ND | Pos | Neg | 1 | 2 | 3 |
| 7 | LG1 | 11 | 4 | 5 | 2 | 0 | 11 | 0 | 0 | 8 | 3 | 0 | 1 | 10 | 0 | 7 | 4 | 9 | 2 | 0 |
| | LG2 | 17 | 3 | 8 | 6 | 0 | 15 | 0 | 2 | 13 | 2 | 2 | 3 | 8 | 6 | 13 | 4 | 9 | 7 | 0 |
| | HG1 | 5 | 0 | 2 | 3 | 0 | 0 | 5 | 0 | 0 | 5 | 0 | 1 | 4 | 0 | 3 | 0 | 0 | 0 | 5 |
| | HG2 | 10 | 0 | 7 | 3 | 0 | 7 | 3 | 0 | 5 | 5 | 0 | 3 | 4 | 1 | 9 | 1 | 0 | 2 | 8 |
| | HG3 | 13 | 0 | 6 | 7 | 0 | 10 | 2 | 1 | 12 | 0 | 1 | 2 | 7 | 2 | 10 | 3 | 0 | 7 | 6 |
| | HG4 | 4 | 0 | 2 | 2 | 0 | 4 | 0 | 0 | 4 | 0 | 0 | 0 | 4 | 0 | 2 | 2 | 0 | 4 | 0 |

It is noted that the HG 1 subgroup is particularly different from the other HG subgroups. One possible reason might be that all samples in it are ER negative. The HG2 subgroup has a mixed ER signature, and the HG3 and HG4 subgroups includes mostly ER positive samples. The standard markers used in clinical diagnosis (shown in Table 1) are not able to distinguish the subgroups (LG1-HG4). Moreover, the 6 subgroups always contain samples in both DCIS and IDC stages from the same patient. This suggests that there is strong heterogeneity in the way different sets of patients progress to the same final stage/grade of disease and that the clustering techniques used here can identify this substructure in the disease pathology. Note also that whereas PCA is able to identify a collection of markers, it could not by itself, reveal the rich stratification of phenotypes found by consensus ensemble k-clustering.

Identification of Significant Characteristic Markers for the LG and HG Subgroups The markers identified for each category below are summarized in Table 2. Note that these are only a few of the markers identified.

Discriminator Markers for the LG and the HG Groups

Using a non-stringent SNR test (permutation p-value p=0.10) 223 gene markers are found which distinguish the group LG from HG. A subset of 10 markers is selected based on their performance on leave-one-out cross-validation experiments for weighted voting (WV) and kNN classification models. The models trained on these 10 markers produced only 1 FP error (DCIS #79) and 1 FN error (DCIS #183) in leave-one-out experiments.

Characteristic Markers for LG

Again, using the SNR test and leave-one-out experiments for WV and kNN models, 10 markers which distinguish the LG samples from all others (HG and N) with 90% accuracy are identified. RBSK, *Homo sapiens* cDNA FL112924 fis, clone NT2RP2004709 and CRIP1 are up-regulated in the LG group, and EYA2, ANXA I, RUNX3, DKFZp762A227, GPRCSB are down-regulated in the LG group.

Characteristic Markers for HG

Here the classification accuracy is 97% for the markers shown in the table with 3 FP and no EN errors. The top markers up-regulated in HG are TRAM, HSPC150, TACC3, CDKN3, UBE2C, and top markers down-regulated in HG are X123, GNG7, SH3BGRL2, LOH11CR2A and *Homo sapiens*, clone IMAGE:3917549 mRNA, partial cds.

Low Grade Substructure

Table 1 shows that both LG1 and LG2 are ER+, PR+ and HER2−, which explains their pathological classification as low grade. The top markers for the LG1 and LG2 subgroups are shown in Table 2. The LG1 cluster had mostly Grade I samples (87%) whereas LG2 cluster had mostly Grade II samples (63%) which identified LG2 as the more aggressive subgrade. The genes that discriminate LG 1 from other low and highgrade subgroups include down-regulated BIRCS (survivin) gene, which inhibits apoptosis and is suggested as a marker of poor prognosis in different cancer types. Two others are ACAA1 and ACOXI enzymes, which are involved in fatty acid metabolism. LG2 markers include 190 genes, among which are many oncogenes, (BCL2 (down, breast cancer poor prognosis marker), RAD5 1 (up), EGFR (up), RUNX3 (up), BCL9 (down) and VAV3 (down)) and tumor suppressor gene NME1 (up).

Tables 2a and b show best characteristic markers for the bca subgroups (top) and for bca progression (bottom). Up-regulated markers in the group are underlined.

TABLE 2a

| | |
|---|---|
| LG vs HG | cDNA DKFZp588G0321, GNG7, MGC4843, *Homo sapiens*, clone MGC:10083, ZNF20, UBE2C, CDKN3, TRAM, KIAA0175, MGC2677 |
| LG vs all | RBSK, *Homo sapiens* cDNA FLJ12924 fis, CRIP1, *Homosapiens*, clone MGC: 26847, ESTs, EYA2, ANXA1, RUNX3, DKFZp762A227, GPRC5B |
| LG1 vs all | PRC1, EYA2, ANXA1, ENO1, IL1RN, DGKD, DKFZP761I2I23, ITGA7, VEGFB, ACAA1 |
| LG2 vs all | KIAA1361, CACNAID, *Homo sapiens* cDNA FLJ12924 fis *Homo sapiens*, clone MGC: 10083 MGC4643, CGI-57, NP25, COL4A2, FLJ20392, 0 |
| HG vs all | TRAM, HSPC150, TACC3, CDKN3, UBE2C, X123, GNQ7, SH3BGRL2, LOH11CR2A, *Homo sapiens*, clone IMAGE: 3917549 |
| HG1 vs all | ESTs, Highly similar to T47163, ESTs, Weakly similar to JC5314 CDC28, CENPA, 0, *Homo sapiens*, clone, MLPH, IGBP1, *Homo sapiens* mRNA; cDNA DKFZp586H021, ZNF175, ESTs |
| HG2 vs all | HEC, FLJ10074, BBM2, MLN64, MGC9753, KIAA0210, SATB1, *Homo sapiens* cDNA FLJ13384 fis, HDAC5, BCL2 |
| HG3 vs all | LOC513321, FLJ22067, UBE2C, PSMD12, H11, GSTP1, ZD52F10, AQP5, KIAA0015, NCALD |
| HG4 vs all | MGC4692 *Homo sapiens* cDNA: FLJ23602 fis ESTs NDUEA2, SNRPB, MGC4248, EFS2, CSDA, PRO2032, TPM2 |

TABLE 2b

| | |
|---|---|
| ALL | PODXL, NTRK2, SH3BGRL2, DMN, MAOA, AEBP1, COL5A2, MMP11, ADAM12, COL6A1 |
| LG | SOX10, *Homo sapiens* cDNA FLJ14368 fis, KLK8, EFS2, MAOA, CDH11, *Homo sapiens* cDNA FLJ32051 fis, AIP-1, COL6A1, AEBP1 |
| LG1 | SOX10, SOX8, JAM2, JTM3, ESTs, FLJ21213, MIG-6, FLJ23293, FLJ10463, LOXL1 |

TABLE 2b-continued

| | |
|---|---|
| LG2 | *Homo sapiens* cDNA FLJ31655 fis *Homo sapiens* cDNA FLJ14368 fis, *Homo sapiens* mRNA for FLJ00074 protein MAOA $$, NPPB, LOC51285, FLJ14987, APBB1, IFI35 |
| HG | LOC118430, SCYD1, PODXL, KIAA1671, ESTs, Weakly similar to A47582, MMP11, TEM1, ADAM12, AEBP1, MGC2577 |
| HG1 | CEACAM6, KIAA0182, PRG5, *Homo sapiens* cDNA FLJ20667 fis, ABCA8, SCAMP3, KIAA0943, HFL1, NUDE1, H2BFQ |
| HG2 | SGCE, TM7SF1, KIAA0819, HAIK1, DNAJB9, MGC4825, ESTs, ANKT, GHRH, IKBKB |
| HG3 | PODXL, CEACAM1, MAOA, *Homo sapiens*, clone MGC: 4552, LOC118430, MMP11, WDR5, KIAA0682, TACC3, *Homo sapiens*, clone MGC: 20766 |
| HG4 | DAB2, ADAR, B7-H3, EVPL, ARPC5, KIAA0375, ESTs, ABCA8, PELI2, IKBKB |

High Grade Substructure

As seen in Table 1, all the samples in the HG1 subgroup are ER and PR negative while those in the HG3 and HG4 subgroups are mostly ER and PR positive. The HG2 samples had mixed ER and PR signatures. The HG1 subgroup, which is the worst prognosis group based on clinical characteristics, has discriminatory markers of oncogenes BCL2 (up), RAD51 (down); GSTP1 (down) gene which leads to cancer susceptibility due to hyper-methylation or polymorphisms, and RRM2 (down). HG2 markers also include up-regulated BCL2 (1.7 fold less up-regulated than in HG1) and down-regulated RRM2. The HG3 markers, include a group of down-regulated genes in chromosomal region 17q23-25 which harbors the ERBB2 amplicon 17q 22.24. These genes are KPNA2 (17q23.1-q23.3), amplified in breast cancer I (AIBCI, 17q23.2), Bcl-2 inhibitor of transcription (BIT1, 17q23.2), hypothetical protein TANC2 (i7q23.3), and two proteosome protein PSMC5 (17q23-Q25) and PSMDI2 (17q24.2).

This suggests the possibility that patients in the HG3 subgroup might have a re-arrangement or deletion of genes around the ERBB2+ gene leading to loss of regulation or function for these genes which might explain the observation that only 15% of HG3 patients are HER2+, while 53% are HER2− and 15% are undetermined. An overall conclusion is that H(G3 has better prognosis than HG1 with the signature (ER+, PR+ and HER2−). The most notable HG4 marker is down-regulated transforming growth factor, beta receptor II (TGFBR2).

Figure 3:
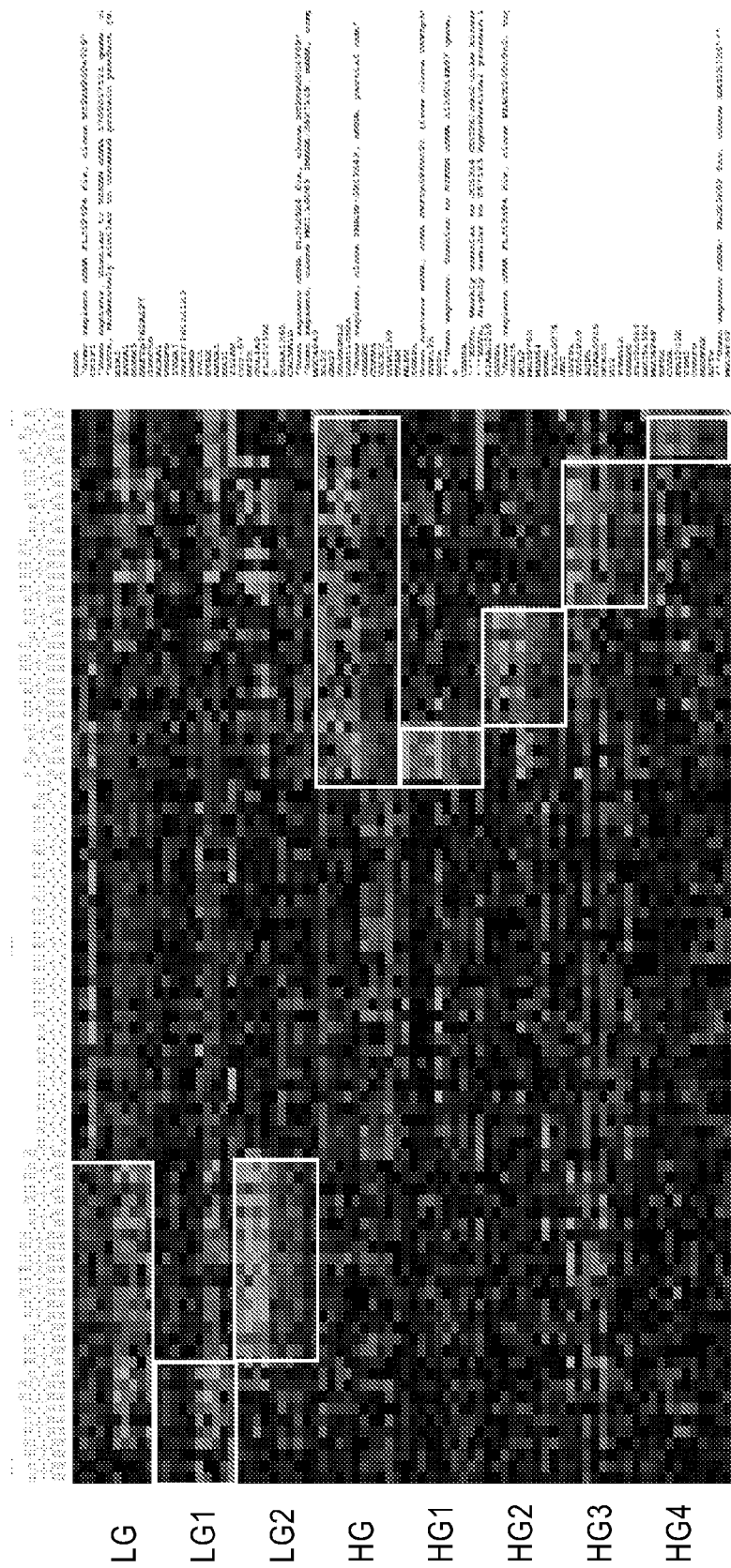
FIG. 3 illustrates a heatmap of the top 10 gene-markers characteristic of each significant phenotype identified in the data of the example.

Mutations in this gene have been associated with the development of various types of tumors. The over-expression of this gene is found to be associated with poor prognosis breast tumors. Overall, gene markers and clinical parameters lead to the conclusion that among the high grade subgroups HG4 is probably the best prognosis group composed of Grade II tumors that are all ER+ and PR+. FIG. 3 presents a heatmap of the top 10 gene markers characteristic of each significant phenotype identified in the data. Dark/light grey represent up/down regulation relative to black. Each set of markers distinguish the samples in the phenotype from all the other samples with an accuracy above 90% in leave-one-out experiments for WV and kNN classification models. The signatures of the subgroups LG1-HG4 stand out clearly. Table 3 presents sensitivity and specificity scores on leave-one-out cross-validation experiments for WV models. Note that the specificity ranges from 92-97%, and the sensitivity from 82-100%.

Table 3 shows accuracy of weighted voting classifiers in distinguishing each group from all other samples. The accuracy scores are computed using leave-one-out experiments. The gene markers for classification are selected as the top genes based on their collective power to accurately discriminate between a group and its complement.

TABLE 3

| Group | Sensitivity | Specificity | Accuracy |
|---|---|---|---|
| LG | 89.29 | 90.77 | 90.32 |
| LG1 | 81.82 | 91.46 | 90.32 |
| LG2 | 100.00 | 90.79 | 92.47 |
| HG | 96.88 | 95.08 | 95.70 |
| HG1 | 100.00 | 96.59 | 96.77 |
| HG2 | 100.00 | 96.39 | 96.77 |
| HG3 | 84.62 | 92.50 | 91.40 |
| HG4 | 100.00 | 94.38 | 94.62 |

Identification of Significant Markers for Breast Cancer Progression

Figure 4:
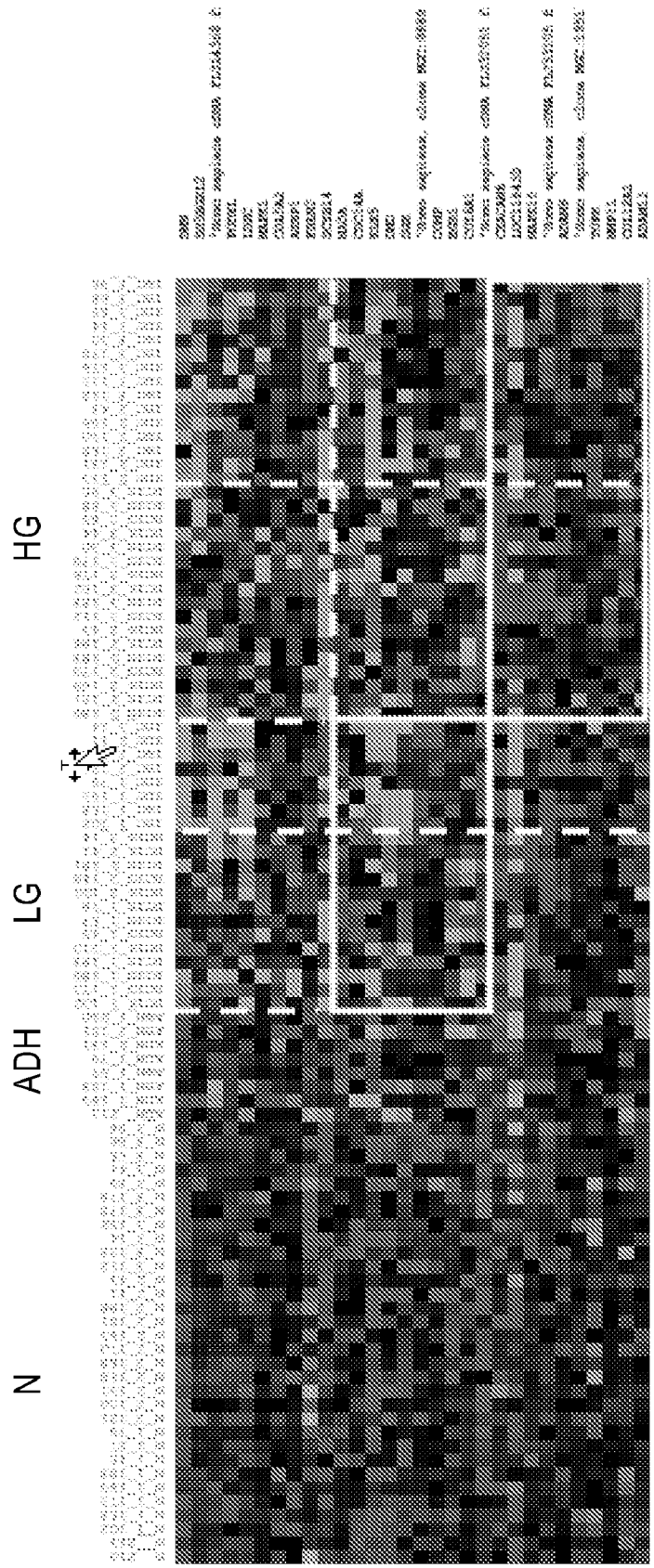
FIG. 4 illustrates the heatmap of the expression levels of the markers group in the samples.
Figure 5:
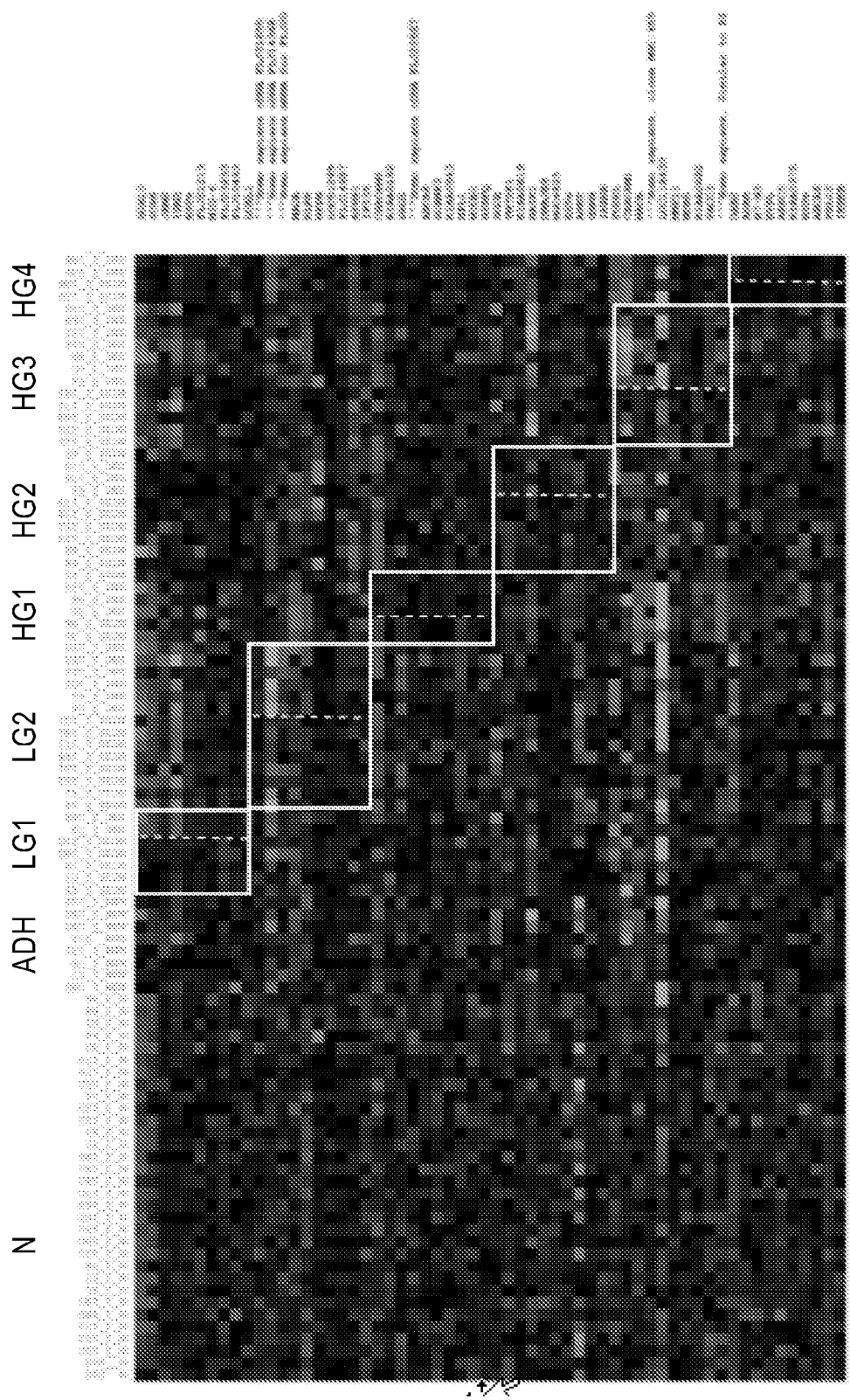
FIG. 5 also illustrates the heatmap of the expression levels of the markers group in the samples.

The progression markers at different levels of granularity in the data are identified and it is found that the progression of the disease from non-invasive to invasive status occurs along different pathways. The top 10 progression markers are also identified within each significant subgroup (Tables 2 a, b). FIGS. 4 and 5 present the heatmaps of the expression levels of these markers. FIG. 4 shows heatmap of the expression level of top progression markers from DCIS to IDC in the low grade and high grade tumor subgroups. The first 10 genes are top markers for DCIS/IDC progression in both LG and HG. Next 10 genes are top markers for progression in LG, and last 10 genes are top markers for progression in HG. FIG. 5 shows heatmap of the expression level of top 10 progression markers from DCIS to IDC for each subgroup, identified in low grade tumor and high grade tumor subgroups. Each subgroup is in a framed box to identify its samples and distinguish gene markers.

Figure 6A:
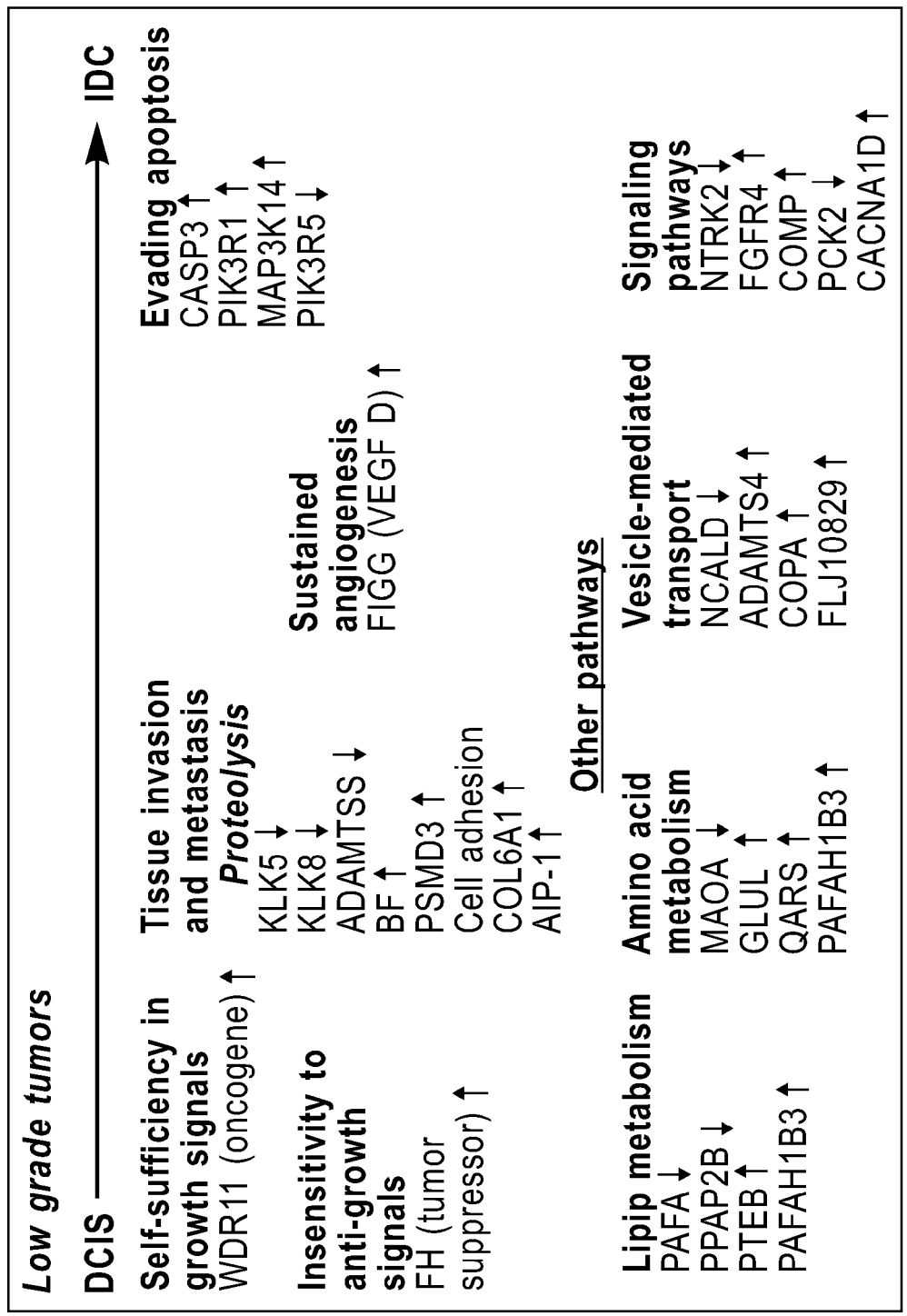
FIGS. 6A and 6B illustrates the summary of the pathways and the genes, which are altered in progression in the low and high-grade group in the example.
Figure 6B:
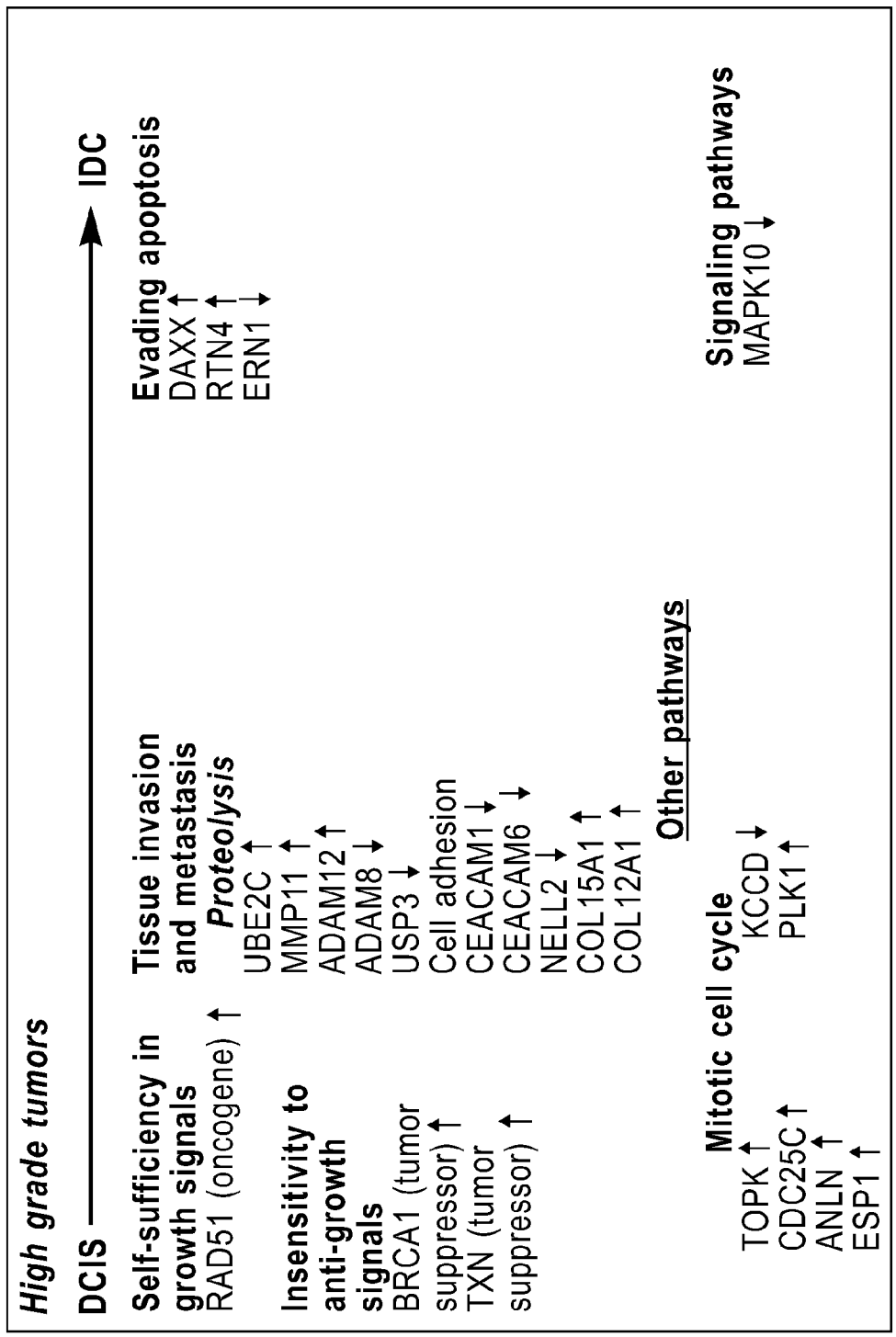

FIGS. 6A and 6B summarizes the pathways and the genes, which are altered in progression in the low and high grade groups. Progression models for low and high grade tumors. Marker genes were replaced into Weinberg categories. Although the exact order of these steps is not known, it has been suggested from other cancers that activation of oncogenes and loss of tumor suppressor genes are usually early events, and induction of angiogenesis is an early to midstage event. The progression in the low-grade groups seems to correlate with changes in metabolic and transportation pathways, while in the highgrade groups it is related to alterations in cell-cycle and signaling pathways. Table 4 presents a summary of the significant pathways involved in the low- and high grade subgroups. The differences between the levels in the DCIS and IDC groups are quite subtle and the accuracy of simple WV models trained to distinguish between DCIS and IDC in each group ranges between 60-70%.

TABLE 4

Enriched progression marker pathways in low and high tumor groups.

| Group | Enriched patways |
|---|---|
| LG | lipid metabolism, transcriptional regulation, vesicle-mediated transport, amino acid and derivative metabolism |

TABLE 4-continued

Enriched progression marker pathways in low and high tumor groups.

| Group | Enriched patways |
|---|---|
| LG1 | small GTPase, mediated signal transduction, intracellular trafficking and vesicular transport |
| LG2 | proteolysis collagens mRNA processing |
| HG | mitotic cell cycle, ATM signaling pathway, Role of BRCA1 BRCA2 and ATR in cancer susceptibility, cell cycle: G2/M checkpoint |
| HG1 | ion transport |
| HG2 | cell cycle proteolysis |
| HG3 | collagens proteolysis |
| HG4 | proteolysis |

Figure 7:
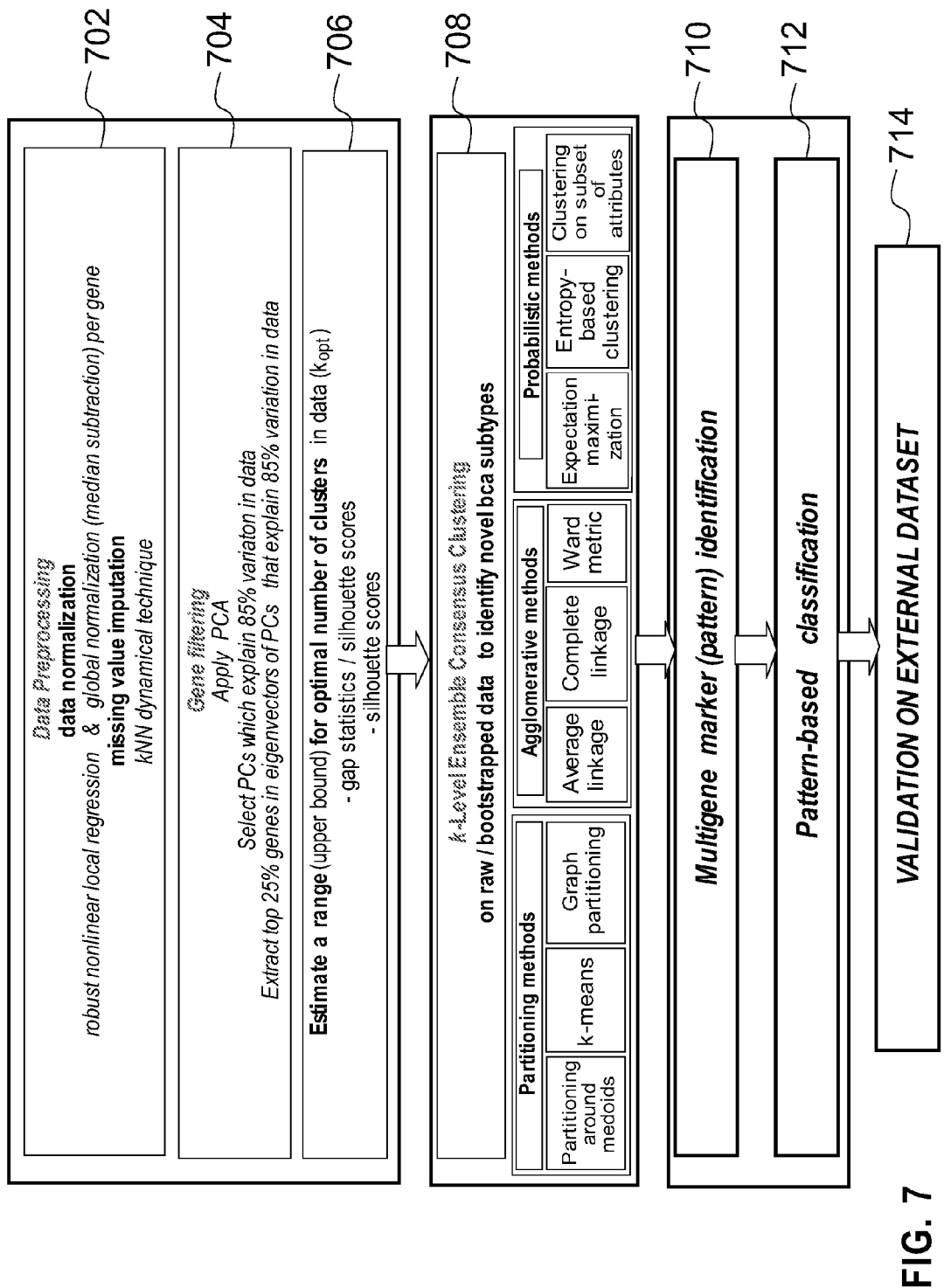
FIG. 7 illustrates the flow chart of the method present disclosure in one embodiment as applied to the breast cancer data.

FIG. 7 illustrates the flow chart of the method present disclosure in one embodiment as applied to the breast cancer data of Ma et al. At 702, the method in one embodiment normalizes the data for example using robust nonlinear local regression and global normalization, and missing values are imputed, that is, generated and filled in. At 704, the method in one embodiment applies PCA to the normalized data. For example, the method in one embodiment selects principal components, which explain 85% variation in data. The method further extracts top 25% genes in eigenvectors of principal components that explain 85% variation in data. At 706, the method in one embodiment estimates a range (upper bound) for optimal number of clusters in data, for example, using gap statistics and/or silhouette scores.

At 708, the method performs k-level ensemble consensus clustering on raw or bootstrapped data to identify novel bca subtypes. K-level ensemble consensus clustering may include but is not limited to partitioning methods, agglomerative methods, and probabilistic methods. At 710, multi-gene markers (pattern) are identified, and at 712, pattern based classification is performed. At 714, validation on external dataset may be performed.

The method of the present disclosure may be implemented and run on a general-purpose and/or special purpose computer or computer system. The embodiments described above are illustrative examples and it should not be construed that the present invention is limited to these particular embodiments. Thus, various changes and modifications may be effected by one skilled in the art without departing from the spirit or scope of the invention as defined in the appended claims.

We claim:

1. A computer-implemented method of finding robust clusters in microarray data comprising:
   identifying patterns of variation in the microarray data;
   applying consensus ensemble clustering to said identified variations; and
   identifying robust clusters,
   applying the consensus ensemble clustering further including creating an agreement matrix across clustering techniques for clusters found from each clustering technique and applying and reapplying simulated annealing to convert the agreement matrix into block diagonal form and to identify the robust clusters along the diagonal.

2. The method of claim 1, wherein the step of identifying patterns includes performing principal component analysis to identify patterns of variation in the data.

3. A computer-implemented method of finding robust clusters in data comprising:
   normalizing a microarray data set;
   identifying attributes of the data set that contribute to most of variation in the normalized data set;
   selecting data having the attributes that contribute to most of the variation in the normalized data set;
   identifying a plurality of clusters from the selected data using consensus ensemble clustering; and
   identifying robust clusters from the plurality of clusters,
   the step of identifying a plurality of clusters from the selected data using consensus ensemble clustering further including creating an agreement matrix across clustering techniques for clusters found from each clustering technique and applying and reapplying simulated annealing to convert the agreement matrix into block diagonal form and to identify the robust clusters along the diagonal.

4. The method of claim 3, wherein the step of identifying data that contribute to most of the variation in the normalized data set includes performing principal component analysis to the normalized data set.

5. The method of claim 3, wherein the step of normalizing includes:
   applying nonlinear local regression to the data set; and
   applying a global normalization procedure to the data set including at least subtracting median of the dataset from the data set.

6. The method of claim 3, wherein the step of normalizing further includes:
   estimating one or more values for one or more missing entries in the normalized data.

7. The method of claim 3, wherein the data set describes genes and the method is used to identify disease.

8. The method of claim 3, wherein the data set includes a plurality of samples of a plurality of genes, and the step of identifying attributes that contribute to most of the variation in the normalized data set includes applying principal component analysis to an expression matrix defined by rows of samples and columns of genes.

9. The method of claim 8, wherein the step of applying principal component analysis includes performing a singular value decomposition of the expression matrix.

10. The method of claim 9, wherein the step of performing a singular value decomposition of the expression matrix includes finding eigenvectors and eigenvalues of the expression matrix.

11. The method of claim 10, further including selecting eigenvectors and eigenvalues accounting for 85% of variation in the normalized data.

12. The method of claim 3, wherein the step of identifying a plurality of clusters includes partitioning the selected data, having the attributes that contribute to most of the variation in the normalized data set, into one or more training set and testing set.

13. The method of claim 12, wherein the step of identifying a plurality of clusters further includes:
   determining an optimum number of clusters on said one or more training set using a metric; and
   validating the optimum number on said one or more testing set.

14. The method of claim 13, further including:
   applying a consensus function to combine one or more clusters in said one or more training set.

15. The method of claim 3, wherein the data set is associated with genes and the method further includes:
   identifying one or more gene markers in the plurality of clusters.

16. The method of claim 15, wherein the step of identifying one or more gene markers in the plurality of clusters includes:

using one or more reference markers identified in the data set; and comparing the one or more reference markers in each of the plurality of clusters.

17. The method of claim 16, wherein said gene markers enable discrimination between a class that represents a group of interest and another class that represents a group of no interest.

18. The method of claim 3, wherein said data set is collected by existing information or collected from at least one clinical sample or combination thereof.

19. The method in claim 3, wherein the method is used to identify a generic profile of a patient in phenotype discovery.

20. A program storage device readable by machine, tangibly embodying a program of instructions executable by the machine to perform a method of finding robust clusters in data comprising:

normalizing a microarray data set;
identifying attributes of the data set that contribute to most of variation in the normalized data set;
selecting data having the attributes that contribute to most of the variation in the normalized data set;
identifying a plurality of clusters from the selected data using consensus ensemble clustering; and
identifying robust clusters from the plurality of clusters,
the step of identifying a plurality of clusters from the selected data using consensus ensemble clustering further including creating an agreement matrix across clustering techniques for clusters found from each clustering technique and applying and reapplying simulated annealing to convert the agreement matrix into block diagonal form and to identify the robust clusters along the diagonal,
wherein a generic profile of a patient in phenotype discovery is identified.

* * * * *